United States Patent
Kube et al.

(10) Patent No.: US 10,350,024 B2
(45) Date of Patent: Jul. 16, 2019

(54) RFID TRANSPONDER FOR A MEDICAL INSTRUMENT AND/OR FOR AN ENDOSCOPE, MEDICAL INSTRUMENT AND/OR ENDOSCOPE, AND ASSEMBLY METHOD

(71) Applicant: Karl Storz SE & Co. KG, Tuttlingen (DE)

(72) Inventors: Raik Kube, Hamburg (DE); Christian Czupalla, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 129 days.

(21) Appl. No.: 15/381,470

(22) Filed: Dec. 16, 2016

(65) Prior Publication Data

US 2017/0172701 A1    Jun. 22, 2017

(30) Foreign Application Priority Data

Dec. 16, 2015    (DE) .......................... 10 2015 016 233
Dec. 8, 2016     (EP) ..................................... 16002611

(51) Int. Cl.
    *G08B 13/14*      (2006.01)
    *A61B 90/98*      (2016.01)
    (Continued)

(52) U.S. Cl.
    CPC .......... *A61B 90/98* (2016.02); *A61B 1/00016* (2013.01); *G06K 19/0723* (2013.01);
    (Continued)

(58) Field of Classification Search
    USPC .............. 340/572.8, 10.1–10.6, 572.1–572.9
    See application file for complete search history.

(56) References Cited

U.S. PATENT DOCUMENTS 5,351,691 A * 10/1994 Brommersma .......... A61B 8/12
                                      600/459
7,414,583 B2 * 8/2008 Choi ....................... H01Q 1/22
                                     343/700 MS
(Continued)

FOREIGN PATENT DOCUMENTS

DE        19723442 A1    2/1998
DE        20012337 U1    10/2000
(Continued)

OTHER PUBLICATIONS

European Search Report Application No. 16002611.8 dated Apr. 24, 2017 7 pages.

(Continued)

*Primary Examiner* — Kerri L McNally
*Assistant Examiner* — Thang D Tran
(74) *Attorney, Agent, or Firm* — Whitmyer IP Group LLC (57) ABSTRACT

An RFID transponder for a medical instrument and/or for an endoscope includes at least one printed circuit board carrying an antenna embodied as at least one conductor track of the printed circuit board and an RFID circuit coupled to the antenna, wherein the at least one printed circuit board has a substantially ring-shaped embodiment and the at least one conductor track is embodied on a radially extending surface of the printed circuit board. A medical instrument and/or endoscope including an RFID transponder, and to an assembly method for a medical instrument and/or endoscope including an RFID transponder.

19 Claims, 4 Drawing Sheets

(51) Int. Cl.
*A61B 1/00* (2006.01)
*H01Q 1/22* (2006.01)
*H01Q 1/27* (2006.01)
*H01Q 1/38* (2006.01)
*H01Q 9/26* (2006.01)
*G06K 19/07* (2006.01)
*G06K 19/077* (2006.01)

(52) U.S. Cl.
CPC ... *G06K 19/0772* (2013.01); *G06K 19/07758* (2013.01); *G06K 19/07786* (2013.01); *H01Q 1/2208* (2013.01); *H01Q 1/273* (2013.01); *H01Q 1/38* (2013.01); *H01Q 9/265* (2013.01)

(56) References Cited

U.S. PATENT DOCUMENTS

| | | | | |
|---|---|---|---|---|
| 7,750,864 B2* | 7/2010 | Hilgers | ............ | G06K 19/07749 343/700 MS |
| 2004/0026411 A1* | 2/2004 | Mucke | ................ | A47L 15/4285 219/543 |
| 2004/0092991 A1* | 5/2004 | Deng | ............... | A61B 17/32002 606/170 |
| 2006/0109121 A1* | 5/2006 | Dishongh | ........ | G06K 19/07749 340/572.1 |
| 2007/0102529 A1* | 5/2007 | Sellew | ................. | G06K 19/041 235/492 |
| 2007/0249901 A1* | 10/2007 | Ohline | ................... | A61B 1/005 600/117 |
| 2007/0290856 A1* | 12/2007 | Martin | ............... | G06K 19/0726 340/572.3 |
| 2008/0030343 A1* | 2/2008 | Raybuck | ................ | A61B 90/90 340/572.8 |
| 2009/0096629 A1* | 4/2009 | Sprowl | ................. | G06K 19/04 340/693.5 |
| 2009/0124215 A1* | 5/2009 | Nysen | ................... | H01Q 1/2275 455/90.1 |
| 2009/0289116 A1* | 11/2009 | Copeland | ............. | G06K 7/0004 235/440 |
| 2010/0007501 A1* | 1/2010 | Yang | ........................ | B01L 3/545 340/572.8 |
| 2010/0151972 A1* | 6/2010 | Lim | ..................... | A63B 57/353 473/406 |
| 2011/0201190 A1* | 8/2011 | Hermes | .................... | C25D 5/02 438/597 |
| 2011/0253792 A1* | 10/2011 | Tuttle | ............... | G06K 19/07749 235/492 |
| 2012/0256806 A1* | 10/2012 | Davidowitz | .......... | G01S 13/751 343/859 |
| 2014/0155696 A1* | 6/2014 | Sakata | ................. | A61B 1/0055 600/138 |
| 2014/0210977 A1* | 7/2014 | Amling | .............. | A61B 1/00006 348/76 |
| 2014/0246472 A1* | 9/2014 | Kimsey | ................ | A61B 17/068 227/175.1 |
| 2014/0246473 A1* | 9/2014 | Auld | .................... | A61B 17/068 227/175.1 |
| 2014/0246476 A1* | 9/2014 | Hall | ..................... | A61B 17/068 227/175.1 |
| 2014/0246479 A1* | 9/2014 | Baber | .................. | A61B 17/068 227/180.1 |
| 2014/0249557 A1* | 9/2014 | Koch, Jr. | ............. | A61B 17/072 606/170 |
| 2015/0036127 A1* | 2/2015 | Konomura | ............. | G01N 21/95 356/237.2 |
| 2015/0085355 A1* | 3/2015 | Krattiger | ............. | G02B 27/0025 359/368 |
| 2015/0333397 A1* | 11/2015 | Buchsbaum | ......... | H01Q 1/2225 343/788 |
| 2016/0081531 A1* | 3/2016 | Yoshie | ............... | A61B 1/00057 73/40 |
| 2017/0308782 A1* | 10/2017 | Burkholder | .......... | G06K 19/077 |

FOREIGN PATENT DOCUMENTS

| | | |
|---|---|---|
| DE | 10010936 A1 | 9/2001 |
| DE | 102011052501 A1 | 2/2013 |
| EP | 2210219 B1 | 6/2012 |
| WO | 2006080615 A1 | 8/2006 |
| WO | 2012074378 A1 | 6/2012 |
| WO | 2015036519 A1 | 3/2015 |

OTHER PUBLICATIONS

German Search Report Application No. 10 2015 016 233.0. dated Oct. 11, 2016 12 Pages.

* cited by examiner

RFID TRANSPONDER FOR A MEDICAL INSTRUMENT AND/OR FOR AN ENDOSCOPE, MEDICAL INSTRUMENT AND/OR ENDOSCOPE, AND ASSEMBLY METHOD

TECHNICAL FIELD

The present invention relates to an RFID transponder for a medical instrument and/or for an endoscope comprising such a transponder, and to an assembly method for a medical instrument and/or endoscope comprising an RFID transponder.

BACKGROUND

A multiplicity of medical instruments are handled in clinical procedures. By way of example, in the context of a surgical operation, the instruments required to this end must be provided, checked and routed to disposal or preparation after use. To this end, it was found to be useful to provide the medical instruments with a marker which facilitates identification and tracking. Here, machine reading of the marker is desirable for the purposes of increasing the efficiency and safety of the procedures.

The practice of providing medical instruments with one-dimensional codes (line code, barcode) or two-dimensional codes, for example matrix codes, which may be read by appropriate optical readers is known. This reading process is however subject to a multiplicity of influences which reduce the reliability of reading. For example, barcodes applied to surgical instruments by means of a laser have often already faded after approximately half a year's use within the scope of operations and are only readable with difficulty or no longer readable at all. Mechanically applied codes lead to the onset of rusting and are subject to similar deterioration.

Furthermore, the use of radiofrequency identification transponders, which are also referred to as RFID transponders or RFID tags, for marking medical instruments, in particular surgical instruments, is known. The RFID tag contains a memory which stores identification data of the instrument, such as a series number, which may be read by means of an electronic reader. However, the available installation space for the integration of an RFID tag into the instrument is tightly delimited in many surgical instruments, particularly in the case of endoscopic instruments. Furthermore, the reading range of the RFID tags, which are usually tuned to the RF (radio frequency) range with an operating frequency of 13.56 MHz and which have a miniaturized structure, is only a few millimeters. Therefore, it is necessary to place the reading head of the reader as closely as possible to the RFID tag for a reliable data transfer. Therefore, the RFID tags of medical or surgical instruments are generally freely accessible and visible from the outside in order to facilitate a correspondingly close approach of the reading head. However, such an RFID transponder arranged on the surface may be mechanically disturbing, or at least be perceived as disturbing, when handling the instrument and may possibly generate surface roughness which makes cleaning the instrument more difficult. Furthermore, such an arrangement of the RFID tag is connected with great manufacturing outlay.

DE 197 23 442 A1 has disclosed an endoscope with a registration device arranged in the endoscope interior, said registration device capturing at least one ambient parameter to which the endoscope is exposed, wherein the information registered by the registration device may be queried from the outside. Together with the stored data, the registration device is able to transfer a unique identification of the endoscope.

In accordance with DE 200 12 237 U1, a transponder in the case of an endoscope is embedded swimming in a recess in the outer surface of the housing of the endoscope. DE 10 2011 052 501 A1 proposes an RFID tag for equipping surgical instruments, said RFID tag comprising a metal frame and an RFID element with an antenna which, spatially, is arranged substantially outside of the metal frame. In accordance with US 2014/0210977 A1, an endoscope system is embodied for wireless transfer of energy and data, wherein an endoscope and a camera head which is couplable to the endoscope each have a transponder/transceiver. Both transponders/transceivers are configured for wireless transmission and reception of signals from one another.

US 2004/0092991 A1 has disclosed a surgical tool system comprising a handpiece and a cutting accessory, wherein an RFID chip is arranged at an inner wall of an external hub of the cutting accessory. The RFID chip is assembled on a small flexible circuit carrying a conductor track forming a coil. A further coil is housed in the handpiece and serves to read and write data into the RFID chip.

EP 2 210 219 B1 has disclosed an RFID tag which may be used in medical applications and has a hermetically sealed and sterilizable embodiment. The RFID tag comprises a printed circuit board assembly comprising a printed circuit board, an RFID circuit, an antenna and a metallic ground plate, wherein the printed circuit board has a first side and a. second side, the printed circuit board carrying the antenna on its first side and the ground plate on its second side and the RFID circuit being coupled to the antenna and the ground plate. The RFID tag further comprises a formed-over housing, which surrounds the printed circuit board assembly and hermetically seals the latter, the housing consisting of a material which is sterilizable and has a dielectric constant between approximately 1 and 5. The antenna may have a folded configuration with a central part extending from the RFID circuit to one end of the printed circuit board and with a pair of oppositely directed arms.

The non-generic WO 2006/080615 A1 has disclosed an eyelet comprising an eyelet base made out of a conductive material, which comprises a ring part attached tightly to an object and a fastening part. The eyelet further comprises an RFID circuit module, which is assembled at the eyelet base in order to use the eyelet base as an antenna. A slot is formed in the eyelet base and the RFID circuit module is electrically connected to parts which are defined by the slot. The likewise non-generic document US 2010/0007501 A1 describes a container, which may be used for receiving medical products and which has a circular RFID tag.

SUMMARY

It is an object of the invention to specify an RFID transponder which is suitable for marking a medical instrument and/or an endoscope, wherein the aforementioned disadvantages are avoided where possible. In particular, the RFID transponder should easily be integratable into a medical instrument or into an endoscope and offer, where possible, a greater reading range and/or a lower angle dependence during readout than the known RFID transponders which are integrated into medical instruments. Furthermore, it is an object of the invention to specify a medical instrument or an endoscope comprising a corresponding RFID transponder and an assembly method for a medical instrument or endoscope comprising an RFID transponder.

This object is achieved by an RFID transponder, by a medical instrument or endoscope including an RFID transponder and by method of assembling a medical instrument and/or endoscope with an RFID transponder, all in accordance with the present invention.

Advantageous developments of the invention emerge from the dependent claims.

An RFID transponder according to the invention, which is also referred to as RFID tag, is embodied to mark a medical instrument and/or an endoscope. In particular, the term "medical instrument" comprises surgical instruments, endoscopic instruments and medical endoscopes. However, the present invention is not restricted to medical instruments or medical endoscopes but instead likewise relates to endoscopes for nonmedical applications. The RFID transponder is embodied to store data which may serve to identify the relevant medical instrument or the endoscope, wherein the data may be captured contactlessly in a manner known per se by means of an electronic RFID reader.

An RFID transponder according to the invention comprises at least one printed circuit board carrying an antenna which is embodied as at least one conductor track applied to the printed circuit board. Therefore, the printed circuit board carries at least one conductor track which is suitable as an antenna of the RFID transponder and, in particular, has a corresponding length and arrangement. The printed circuit board is preferably manufactured from a material with a dielectric constant between approximately 4 and 80. The printed circuit board may have flexible embodiment. Furthermore, the RFID transponder according to the invention comprises an RFID circuit which is coupled directly or indirectly to the antenna, i.e. with or without interposing one or more further electrical or electronic components. Here, the RFID circuit is coupled to the antenna in such a way that transfer of the identification data stored in a memory of the RFID circuit to an external receiver such as e.g. a corresponding RFID reader is possible. Furthermore, the reception of data and/or an electric power supply of the RFID circuit may be possible by way of the antenna. The transponder may have further components, for example one or more further printed circuit boards, a dedicated energy source such as a battery, and/or a housing.

According to the invention, the at least one printed circuit board has a substantially ring-shaped embodiment. The at least one printed circuit board therefore forms a closed ring, or else a ring with a break, which may be e.g. circular, oval or elliptical. Preferably, the at least one printed circuit board forms an approximately circular ring. The antenna is formed by the at least one conductor track applied to the substantially ring-shaped printed circuit board, wherein the conductor track is embodied on a radially extending area of the printed circuit board in relation to a central axis or an axis of symmetry of the substantially ring-shaped printed circuit board. The radially extending area is e.g. an area lying parallel to the plane of the ring, or in the plane of the ring, or else an approximately helical area. The at least one conductor track is in particular planar and embodied on a surface of the printed circuit board lying parallel to, or in, the ring plane. Preferably, the RFID transponder overall is embodied corresponding to the form of the printed circuit board, likewise substantially ring-shaped, for example oval, elliptic or circular-ring-shaped, and optionally includes further components such as e.g. further printed circuit boards and/or a housing.

A space-saving housing in a medical instrument or in an endoscope is facilitated as a result of the at least one printed circuit board which carries the antenna having a substantially ring-shaped embodiment and hence as a result of the transponder, overall, possibly having a ring-shaped embodiment. In particular, a central opening, which may hold one or more working channels and/or an optical system when integrated into a medical instrument or into an endoscope and which is surrounded or largely surrounded by the printed circuit board or the transponder, is present on account of the ring-shaped configuration of the at least one printed circuit board or of the transponder overall. Further, this facilitates a particularly advantageous configuration of the antenna of the RFID transponder. In particular, housing an antenna within the medical instrument or within the endoscope, said antenna also being suitable for a reading distance of e.g. several centimeters, is facilitated by virtue of the at least one printed circuit board which carries the antenna having a substantially ring-shaped embodiment. This does not require a fundamental reconstruction or an enlargement of the medical instrument or of the endoscope.

Preferably, the RFID transponder is embodied as a passive transponder. Such a passive transponder does not have a dedicated energy source and is supplied with the electrical energy required for the data transfer in a manner known per se, in particular by the reader during a reading process. This facilitates a simple and cost-effective configuration of the RFID transponder, the functionality of which moreover is not restricted by the service life of a dedicated energy source.

More preferably, the RFID transponder is embodied for the UHF frequency range. Hence, to the frequency for the data transfer and, optionally, for the energy transfer preferably lies in the range from 865 to 868 MHz, in particular at approximately 866.5 MHz. As result of this, a reading distance of several centimeters, for example approximately 30 cm, is achievable.

In accordance with one preferred embodiment of the invention, the at least one printed is circuit board is embodied as a ring with one break, preferably as a circular ring with one break; however, the at least one printed circuit board may also form, for example, an oval or elliptical ring with a break. In accordance with this embodiment, the printed circuit board is therefore embodied approximately as a ring or circular ring which has an e.g. radially aligned slot. The slot only assumes a small part of the circumference of the printed circuit board, for example less than one quarter of the circumference, in particular less than one tenth of the circumference, particularly preferably less than one hundredth of the circumference. Preferably, the printed circuit board is embodied as a plane printed circuit board. The ends formed by the break in the circular ring need not be flush with one another. In particular, the printed circuit board may, for example, have the form of a snap ring. Further preferably, the RFID transponder overall is likewise embodied as a ring with one break, preferably in accordance with the form of the printed circuit board as a circular ring with one break which, for example, may have the form of a snap ring. Here, the ends of the RFID transponder are separated by a gap which only assumes a small part of the circumference of the RFID transponder, for example less than a quarter of the circumference, in particular less than one tenth of the circumference, particularly preferably less than one hundredth of the circumference; the ends of the RFID transponder may also lie next to one another. As a result of the printed circuit board or the transponder being embodied as a circular ring with a break, assembly of the printed circuit board or the transponder in a ring-shaped groove is facilitated in a simple manner, said ring-shaped groove, for example, being arranged on an outer or inner side of a ring-shaped or pipe-shaped component of a medical instrument or an endoscope, in particular on an inner side of an eyepiece cup of an endoscope.

The antenna is preferably embodied as a dipole, particularly preferably as a ring dipole which is arranged on both sides of the break in the approximately circular-ring-shaped printed circuit board. Here, coupling of the antenna with the RFID circuit may be effected in a region of the printed circuit board which, in relation to the central axis or axis of symmetry of the circular ring, is arranged approximately opposite the break. The region where the antenna is coupled to the RFID circuit is also referred to as "feed". As a result of the antenna being embodied as a dipole, in particular as a ring dipole, a particularly advantageous use of the area of the at least one printed circuit board available for attaching the at least one conductor track serving as an antenna is facilitated.

Preferably, the antenna is embodied as a conductor track which is folded, at least in sections. Attaching a conductor track or antenna to the printed circuit board, the length of which conductor track or antenna is greater than the length of the printed circuit board as measured along the circumference of the ring, is facilitated by the conductor track, which forms the antenna, being folded at least in sections. As a result of this, an improved adaptation of the antenna to an operating frequency, for example to the UHF range, and hence a longer range, may be facilitated.

In accordance with a particularly preferred embodiment of the invention, the antenna is embodied as a Morgain dipole, which is preferably curved in a ring-shaped manner. Such a Morgain dipole may be formed by two twice-folded planar conductor tracks which extend along the ring-shaped printed circuit board. In particular, these may originate at a feed, which lies approximately opposite to the break, and each extend close to the break, reach back to close to the feed and once again extend close to the break. The embodiment of the antenna as a combination of a ring dipole with a Morgain dipole facilitates matching the antenna to the form of the printed circuit board if the latter is embodied as a ring with a break and, moreover, improved matching of the antenna length to the dimensions of the substantially ring-shaped printed circuit board, which are restricted in medical instruments or endoscopes by the available installation space. Particularly in the case of dimensions suitable therefor, for example in the case of a predetermined inner diameter of the substantially ring-shaped RFID transponder of approximately 1 cm and a ring width of approximately 3 mm, the antenna length may be selected in such a way that a resonant frequency in the UHF range is facilitated. As a result, a further increase in the reading distance and/or matching to a desired working frequency may be obtained.

Preferably, the RFID circuit is coupled to the antenna by way of a coupling loop. The coupling loop may be embodied as a further conductor track, in particular as a planar conductor track, on the at least one printed circuit board. By way of example, the RFID circuit may be embodied as an integrated circuit (IC) and integrated into the coupling loop. As a result of the RFID circuit being coupled to the antenna by way of a coupling loop, improved impedance matching and hence an increase in the range are facilitated. Furthermore, a reactive component of the impedance (reactance) of the RFID circuit may be compensated by suitable selection of the length of the coupling loop.

In accordance with a particularly preferred embodiment, the printed circuit board has a first side and the second side, which may also be referred to as upper side and lower side or as front side and rear side. In accordance with this embodiment, the antenna or the at least one conductor track forming such antenna is arranged on the first side or upper side and the coupling loop, which may likewise be embodied as a conductor track, is arranged on the second side or lower side of the printed circuit board. Preferably, the printed circuit board in each case has plane surfaces on the upper side and the lower side, said surfaces being parallel to a ring plane or perpendicular to the central axis of the printed circuit board, and the conductor tracks forming the antenna and the coupling loop are planar conductor tracks. Furthermore, the RFID circuit may also be arranged on the lower side and, in particular, be integrated into the coupling loop. In this way, a particularly space-saving arrangement may be created.

Preferably, the antenna and the coupling loop on the first side and the second side of the at least one printed circuit board are arranged substantially opposite one another. In a particularly preferred manner, an outer respectively conductor track and an inner conductor track of the antenna and of the coupling loop are congruent, at least in regions, as seen perpendicular to the area of the at least one printed circuit board. As a result of this, particularly effective coupling of the coupling loop and the antenna is facilitated.

Preferably, the distance between the antenna and the coupling loop is matched for compensating an active component (resistance) of the impedance of the RFID circuit. The distance between the conductor tracks forming the antenna and the coupling loop, which are each embodied in a substantially planar manner, is determined by the thickness of the printed circuit board measured in the axial direction, particularly if said antenna and coupling loop lie opposite one another on the first side and the second side of the at least one printed circuit board. Hence, improved impedance matching and hence a further improvement in the transmission and reception properties of the transponder are possible by way of an appropriate selection of the thickness of the printed circuit board.

Furthermore, it is preferable for the coupling loop to be offset in relation to the antenna, i.e. arranged asymmetrically in relation to the latter, in the circumferential direction. In particular, in relation to the central axis of the at least one printed circuit board embodied as a circular ring with a break, the coupling loop does not lie exactly opposite the break but it is displaced in relation thereto on one side of the printed circuit board. Such a shift in the feed may obtain a compensation of an active component of the impedance of the RFID circuit, and so improved impedance matching and hence an improvement in the transmission and reception properties of the transponder are likewise achievable.

In accordance with a particularly preferred embodiment, the transponder has a hermetically sealed housing which surrounds the at least one printed circuit board with the antenna and the RFID circuit and, optionally, the coupling loop and possible further components of the transponder and which is preferably likewise embodied in the form of a circular ring which is closed or has a break in accordance with the at least one printed circuit board. The housing preferably has a dielectric constant in the range between approximately 1 and approximately 5 in order to facilitate advantageous transmission and reception properties of the transponder. Furthermore, the housing may be produced from a medically approved material and embodied to be insensitive in relation to chemical, physical and thermal influences which occur during the usual sterilization methods. Furthermore, it is preferable for the components of the transponder, in particular the components arranged on the at least one printed circuit board, to have, at least approximately, the same coefficient of thermal expansion. In a particularly preferred manner, the housing and the transponder overall are embodied in such a way that these are not damaged by the temperatures and pressures occurring during autoclaving.

A medical instrument and/or endoscope according to the invention comprises an RFID transponder embodied as described above, said RFID transponder, in particular, being integrated into the medical instrument or endoscope in a proximal end region thereof (i.e. close to the user). An identification of the medical instrument or the endoscope is facilitated in a simple and reliable manner by virtue of the medical instrument or the endoscope comprising an RFID transponder according to the invention.

Preferably, the RFID transponder is integrated into an eyepiece cup of an endoscope in such a way that the RFID transponder surrounds a beam path of the endoscope in a substantially ring-shaped manner. Therefore, the beam path of the endoscope extends through a central opening of the RFID transponder surrounded or largely surrounded by the printed circuit board or the transponder. In particular, the printed circuit board, which is embodied in the substantially ring-shaped manner, for example as a circular ring with a single break, surrounds the beam path of the endoscope and is e.g. arranged approximately symmetrically in relation to an optical axis of the endoscope. The beam path of the endoscope is defined by the optical system of the endoscope and also comprises the light path in the region of the window of the eyepiece. Thus, the transponder may e.g. be arranged in such a way that it surrounds the window of the eyepiece, i.e. that it is arranged radially on the outside around the latter. In particular, the RFID transponder is housed in the interior of the eyepiece cup. This aspect of the invention uses the fact that an RFID transponder according to the invention is suitable, in particular, for integration into an eyepiece cup of an endoscope in respect of form, dimensions, reading range and frequency range or may easily be adapted thereto. In a manner known per se, the endoscope may furthermore comprise a shank, an optical system and, optionally, an endoscope head, with the eyepiece cup being arranged at a proximal end of the shank or at the endoscope head. By way of example, the RFID transponder may be inserted into a groove of the eyepiece cup circulating on the inside or into an insert part arranged on an inner side of the eyepiece cup. Alternatively, the RFID transponder may be cast into the eyepiece cup, which may already take place during the production of the eyepiece cup by way of injection molding. The RFID transponder is preferably not visible from the outside. What may be achieved in a simple manner as a result of the RFID transponder being integrated into the eyepiece cup which, as a rule, consists of a non-metallic material, in particular of a plastic suitable for medical purposes, is that the RFID transponder is not surrounded by metallic components and has at least sufficient distance from inner metallic areas of the endoscope such that the signal and energy transfer from or to the RFID transponder are not significantly impaired. In a corresponding manner, instead of being integrated into an eyepiece cup, the RFID transponder may be integrated into a nonmetallic housing of an endoscope head of an endoscope. The RFID transponder may likewise be integrated in a corresponding manner in a component of a medical instrument, said component consisting of a nonmetallic material.

In accordance with a method according to the invention for assembling a medical instrument and/or endoscope comprising an RFID transponder, an RFID transponder which, as described above, is embodied as a ring with a break, in particular as a circular ring with a single break, is provided. At least one component of the medical instrument or of the endoscope is produced with a ring-shaped groove with dimensions sufficient for the RFID transponder. Thereupon, the RFID transponder is inserted into the groove, in particular in the style of a snap ring. Preferably, the groove is embodied as a circumferential groove on an inner side of a component. For insertion purposes, both ends of the RFID transponder are pressed together against the elastic restoring force of the printed circuit board and of the housing and brought into an overlapping arrangement; thereupon, part of the circumference of the RFID transponder is inserted into the groove, whereupon the remaining regions of the circumference and the two ends spread on account of the elastic restoring force and latch into the groove. Preferably, the groove is embodied on an inner side of an eyepiece cup of an endoscope and the eyepiece cup is placed onto a proximal end region of a housing of the endoscope after inserting the RFID transponder, and fixed at said position. As a result, an RFID transponder may be integrated into a medical instrument or into an endoscope in a simple and reliable manner.

It is understood that the features mentioned above and the features yet to be explained below may be used not only in the respectively specified combination, but also in other combinations or on their own, without departing from the scope of the present invention.

BRIEF DESCRIPTION OF THE DRAWINGS

Further aspects of the invention emerge from the following description of preferred exemplary embodiments and from the attached drawing. In detail.

DETAILED DESCRIPTION

Figure 1:
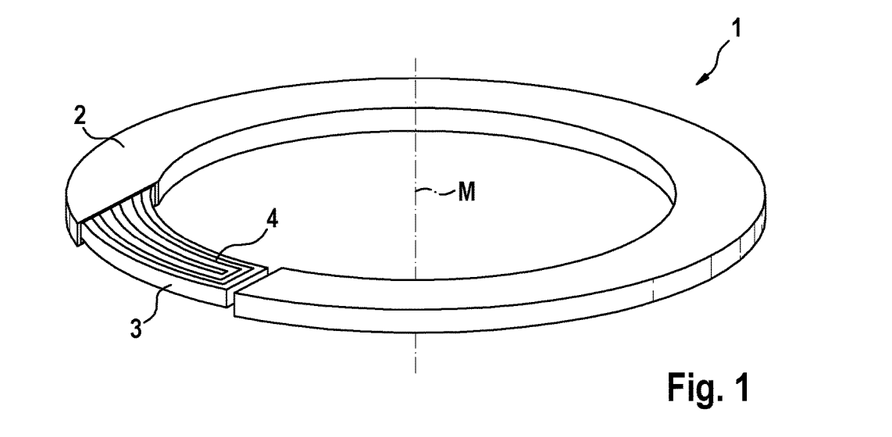
FIG. 1 shows, in an oblique view of the upper side, an exemplary embodiment of an RFID transponder according to the invention, with the housing being partly cut open.

As depicted in the oblique view, shown in FIG. 1, of an RFID transponder 1 embodied in accordance with one exemplary embodiment of the invention, the RFID transponder 1 overall has the form of a plane circular ring which is interrupted by a gap extending in the radial direction. The labels "radial" and "axial" relate to the central axis M of the circular ring indicated in FIG. 1. On all sides, the surface of the RFID transponder 1 is formed by a housing 2 which consists of a material which may be used for medical applications. As may be identified in the cut-open region of the housing 2, a printed circuit board 3 is received in the interior of the housing 2, said printed circuit board carrying a conductor track 4 on the upper side thereof, said conductor track forming the antenna of the RFID transponder 1.

Figure 2:
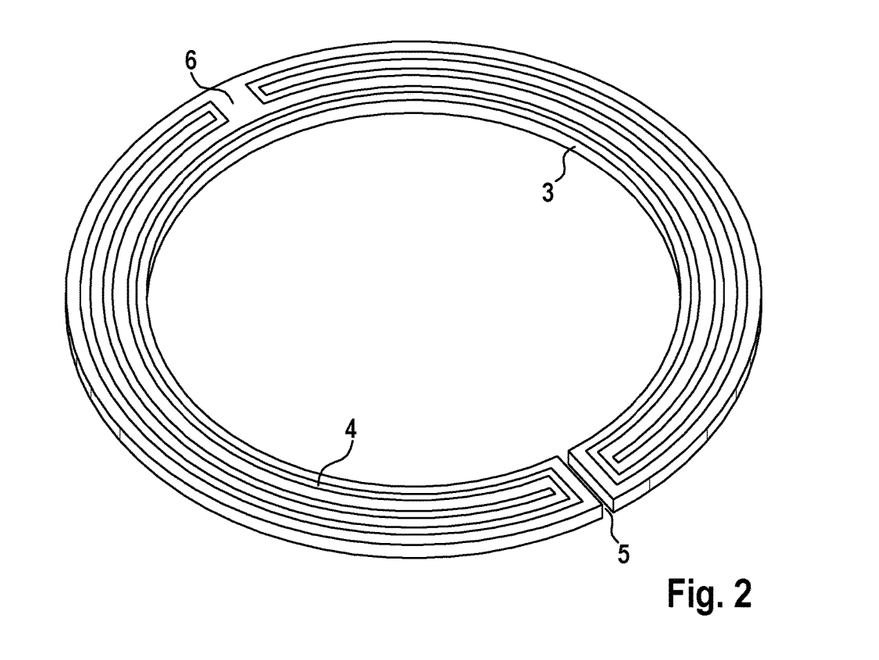
FIG. 2 shows the RFID transponder in accordance with FIG. 1, likewise in an oblique view of the upper side, but without a housing.

The printed circuit board 3 is shown without the housing 2 in FIG. 2. As depicted in FIG. 2, the printed circuit board 2 has the form of a plane circular ring which is interrupted by the gap 5 extending in the radial direction. The conductor track 4 extending on the upper side of the printed circuit hoard 3 represents a Morgain dipole which is curved in a ring-shaped manner. Proceeding from a central region 6 of the printed circuit board 3, arranged opposite the gap 5 in relation to the central axis of the circular ring, the conductor track 4 runs symmetrically on both sides of the central region 6 in the vicinity of the inner edge of the printed circuit board 3 up to near the gap 5, from there it runs back to near the central region 6 in the vicinity of the outer edge of the printed circuit board 3 and from there it once again runs up to near the gap 5 approximately in the center between the inner edge and the outer edge. Hence, the conductor track 4 represents a combination of a ring dipole and a shortened Morgain dipole and in each case forms one and a half turns of a plane coil on both sides of the central region 6.

Figure 3:
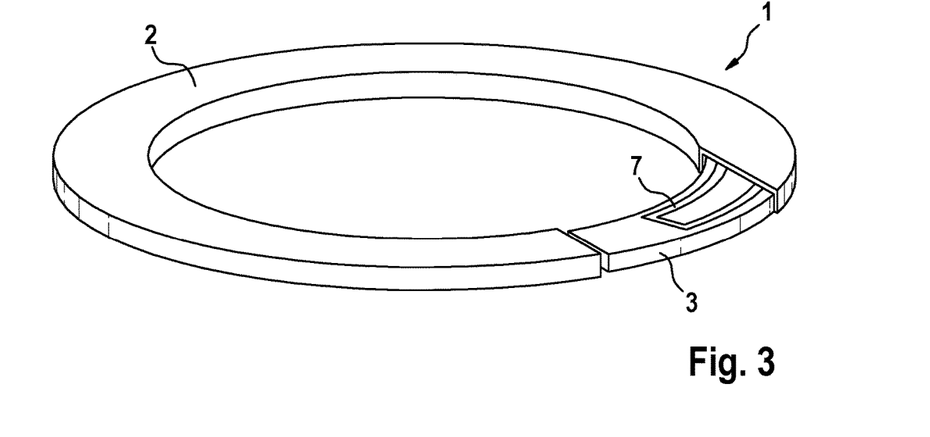
FIG. 3 shows the RFID transponder in accordance with FIG. 1 in an oblique view of the lower side, with the housing being partly cut open.
Figure 4:
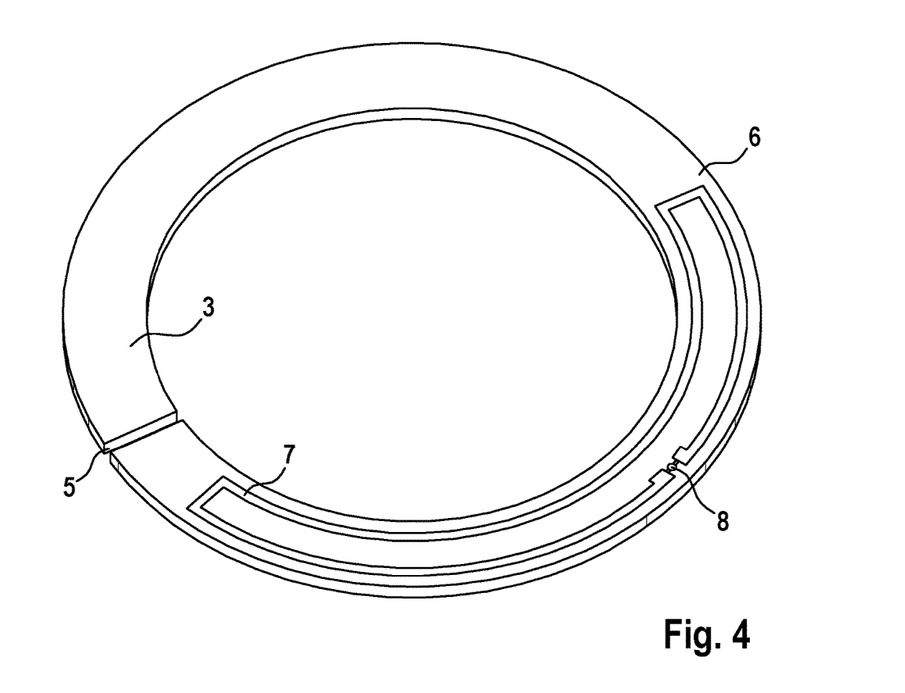
FIG. 4 shows the RFID transponder in accordance with FIG. 1, likewise in an oblique view of the lower side, but without housing.

FIGS. 3 and 4 show, in a corresponding manner, the lower side of the RFID transponder 1 with the partly cut open housing 2 and without the housing 2. On its lower side, the printed circuit board 3 carries a further conductor track 7 which forms a coupling loop. Switched between the ends of the coupling loop there is an RFID circuit 8, which is embodied as an integrated circuit (IC) or as RFID chip. The conductor track 7 runs as a loop along the inner and outer edge of the printed circuit board 3, but only in a portion of the length of the printed circuit board 3. In the shown example, the coupling loop formed by the conductor track 7 extends over almost half of the length of the printed circuit board 3, for example from a region near the gap 5 to the central region 6 of the printed circuit board 3 lying opposite thereto. The housing 2 (see FIGS. 1 and 3) also encloses the end sides of the printed circuit board 3 which adjoin the gap 5; the gap of the RFID transponder 1 is therefore slightly narrower than the gap 5 of the printed circuit board 3.

In the depicted exemplary embodiment, the ends of the printed circuit board 3 separated by the gap 5 lie opposite one another. Deviating herefrom, the ends may also be offset from one another in the axial direction, wherein the printed circuit board 3 may have the form of a helix. The same applies to the RFID transponder 1 overall; the latter may therefore have a form similar to a snap ring. Since the printed circuit board 3 and the housing 2 are flexible, at least to a restricted extent, such an offset of the ends may be achieved at least by exerting an appropriate force, said offset facilitating driving into a groove, like in the case of a snap ring.

By an appropriate configuration of the conductor track 4, the length of the antenna is matched to an operating frequency of the RFID transponder 1 in the UHF range. Furthermore, the impedance of the antenna is matched to that of the RFID circuit 8 by the configuration of the conductor tracks 4, 7 and by the selection of the thickness of the printed circuit board 3. The impedance of conventional RFID chips is approximately 20-200 ohm. The reactive component of the impedance of the RFID circuit 8 is compensated by a suitable selection of the length of the coupling loop. Here, the active component is matched by the offset of the coupling loop from the central region 6 in the circumferential direction of the printed circuit board 3 (feed displacement) and, moreover, by a suitable selection of the thickness of the printed circuit board 3, which defines the distance between the upper side and the lower side of the printed circuit board 3 and hence defines the axial distance between the conductor tracks 4, 7, i.e. between the antenna and the coupling loop.

In the exemplary embodiment shown in FIGS. 1 to 4, the RFID transponder 1 has e.g. an inner radius of approximately 10.5 mm, an outer radius of approximately 11.9 mm and a thickness, as measured in the axial direction, of approximately 1 mm or less. The operating frequency of the RFID transponder 1 lies in the UHF frequency range (865-868 MHz). On account of the described configuration of the antenna and of the coupling loop, a reading range of approximately 30 cm with a small angle dependence may be achieved.

Figure 5:
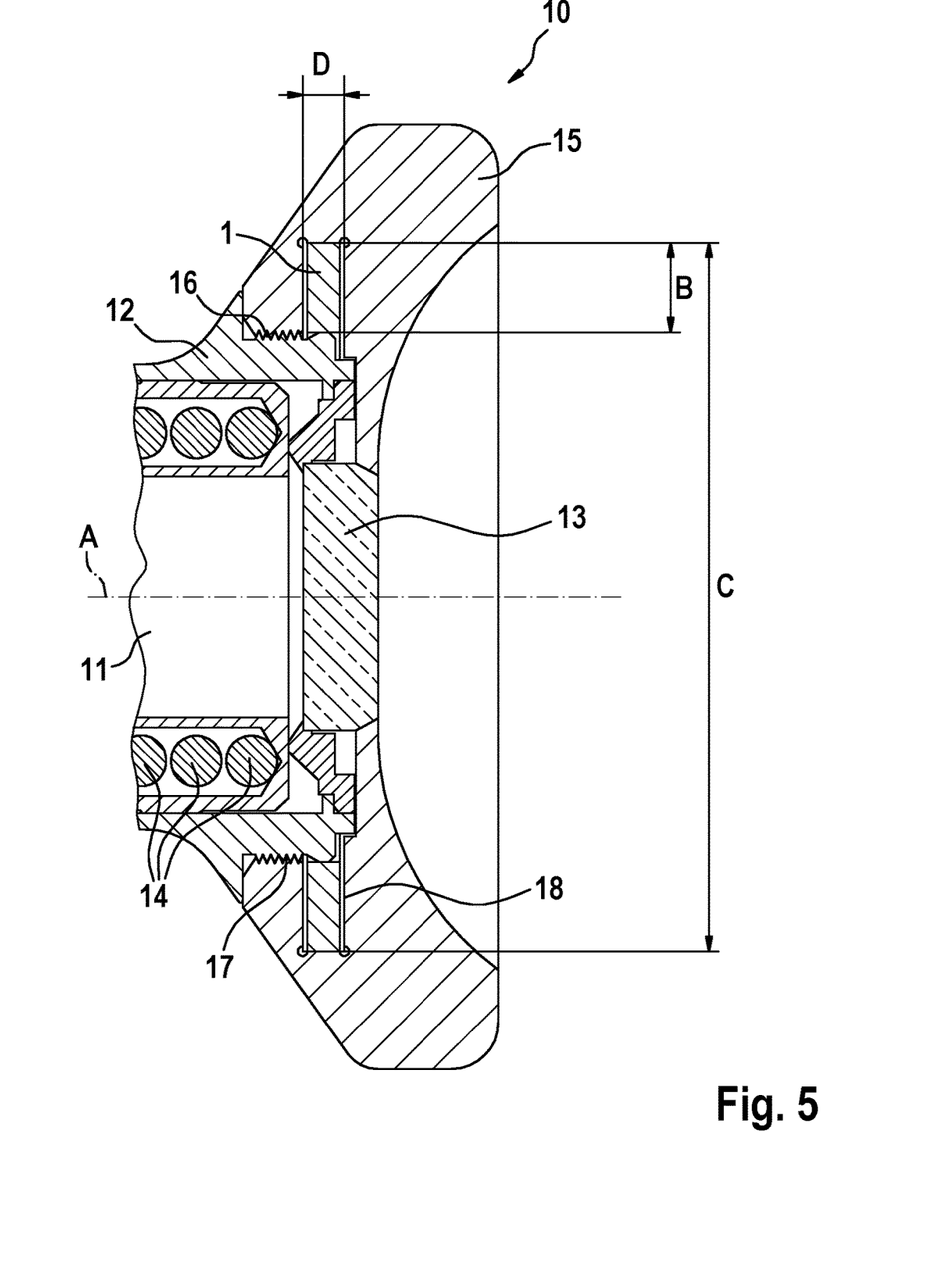
FIG. 5 shows a longitudinal section of the proximal end region of an endoscope according to the invention in accordance with a first exemplary embodiment.

FIG. 5 shows a first exemplary embodiment of an endoscope 10 according to the invention with an integrated RFID transponder 1, the latter being embodied in accordance with the exemplary embodiment depicted in FIGS. 1 to 4. FIG. 5 only depicts the proximal end region of the endoscope 10 in a longitudinal section. The interior 11 of the endoscope 10 is surrounded in a hermetically sealed manner by an endoscope housing 12, which is formed from a plurality of components connected to one another in a fluid-fight manner and which is terminated at the proximal end by a window 13. Furthermore, in a manner known per se, the endoscope 10 has an elongate shank, which is not depicted in FIG. 5 and which is connected in a fluid-tight manner with the endoscope housing 12 and in which an objective and an image forwarding means, formed for example by relay lens systems, for forwarding to the proximal end region the image generated by the objective are arranged. Furthermore, the optical system of the endoscope comprises an eyepiece optics unit for observing the image forwarded by the image forwarding means. Components of the eyepiece optics unit and, optionally, of the image forwarding means are received within the interior 11 (not depicted in FIG. 5). Furthermore, desiccant elements 14 are arranged in the interior 11. FIG. 5 further indicates a longitudinal axis A of the endoscope 10, said longitudinal axis also being the axis of symmetry of the optical system. The RFID transponder 1, which is embodied as a circular ring with a single break in accordance with FIGS. 1 to 4, surrounds the beam path of the endoscope 10, in particular the window 13 of the eyepiece, in a ring-shaped manner and is arranged symmetrically with respect to the longitudinal axis A.

In order to ease the visual observation of the image forwarded by the image forwarding means through the window 13 and optionally in order to connect an endoscopic camera, the endoscope 10 has an eyepiece cup 15 at the proximal end thereof. Said eyepiece cup is screwed onto a male thread 16 formed in the proximal end region of the endoscope housing 12 and, to this end, has an appropriate female thread 17. On the proximal side of the female thread 17, the eyepiece cup 15 has, on the inside, a circumferential groove 18 in which the RFID transponder 1 is inserted. The dimensions of the groove 18 correspond to the external dimensions of the RFID transponder 1 or are slightly larger. In the depicted exemplary embodiment, the groove 18 has a depth B=3 mm, a diameter C=24 mm measured on the base of the groove and axial width D=1.2 mm. The central axis of the substantially ring-shaped RFID transponder 1 approximately coincides with the longitudinal axis A of the endoscope 10. The integration of the RFID transponder 1 into the endoscope 10 does not cause any change in the outer contour of the endoscope 10, in particular it does not cause an enlargement of a portion of the endoscope 10 and does not cause surface roughness. The RFID transponder 1 is not visible from the outside, wherein a reading range of e.g. 30 cm is achievable on account of the described configuration with an operating frequency in the UHF range.

When producing the endoscope 10, the eyepiece cup 15 is, for example, turned from a solid block of polyether ether ketone (PEEK), wherein the female thread 17 and the groove 18 are introduced. Then, the RFID transponder 1 is inserted into the groove 18 in the style of a snap ring. Finally, the eyepiece cup 15 is screwed onto the male thread 16 of the endoscope housing 12 with the female thread 17 thereof and fixed, for example by adhesive bonding.

Figure 6:
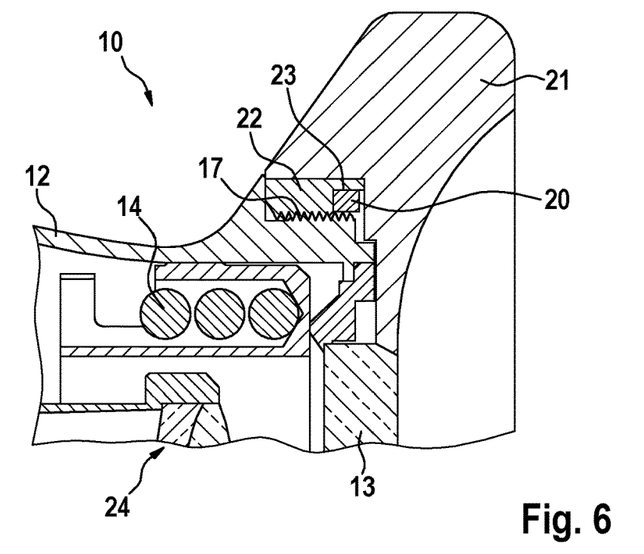
FIG. 6 shows a unilateral longitudinal section of the proximal end region of an endoscope according to the invention in accordance with a second exemplary embodiment.
Figure 7:
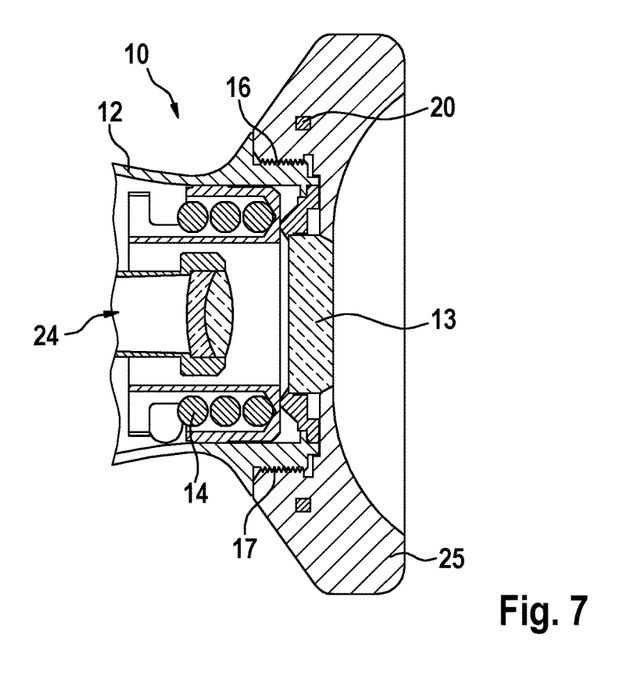
FIG. 7 shows a longitudinal section of the proximal end region of an endoscope according to the invention in accordance with a third exemplary embodiment.

FIGS. 6 and 7 depict, in an exemplary manner, two further installation options for an RFID transponder 20 according to the invention in the proximal end region of an endoscope 10 or in an eyepiece cup 21, 25. Here, the RFID transponder 20 may be embodied like the RFID transponder 1 as described above, but it may also be embodied as a closed circular ring without a break. In the latter case, the printed circuit board may also represent a closed circular ring, wherein the antenna may be embodied as described above (see FIGS. 1, 2) or else may be embodied in a manner known per se by a planar, approximately spirally circulating coil on the upper side of the printed circuit board. An RFID transponder which forms a closed ring and in which the antenna is formed by an approximately spirally circulating coil may have a smaller radial width on account of the greater length of the corresponding conductor track available in this case. For the installation in accordance with FIG. 5, such an RFID transponder must be sufficiently flexible in order to be able to be folded into the groove 18 for insertion purposes. This is not necessary for the installation in accordance with FIGS. 6 and 7 described below.

In accordance with the second exemplary embodiment of an endoscope 10 according to the invention depicted in FIG. 6, the eyepiece cup 21 has a ring-shaped insert part 22 which carries the female thread 17 for screwing onto the proximal end of the endoscope housing 12. By way of example, the insert part 22 is securely connected to the eyepiece cup 21 by way of adhesive bonding. At the proximal end of the insert part 22, the latter has, on the inner side, a recess 23 in which the RFID transponder 20 is inserted. During assembly, the ring-shaped RFID transponder 20 is initially inserted into the recess 23 in the insert part 22 and it is then inserted into the eyepiece cup 21 turned e.g. from a PEEK block, and connected to the latter. Thereupon, the assemblage of eyepiece cup 21, insert part 22 and RFID transponder 20 is screwed onto the proximal end of the endoscope housing 12. In FIG. 6, the optical system 24 of the endoscope 10 is also indicated in addition to the desiccant elements 14.

In the third exemplary embodiment of the endoscope 10 depicted in FIG. 7. the RFID transponder 20 is cast into the eyepiece cup 25. By way of example, this may occur directly in the injection molding process during which the eyepiece cup 25 is produced.

Similar to what was described in relation to FIG. 5, the eyepiece cup 25 is screwed onto the male thread 16 of the endoscope housing 12 by means of a female thread 17. The optical system 24 of the endoscope 10 is also indicated in FIG. 7. Otherwise, the endoscope 10 according to the second and third exemplary embodiments is embodied as described in relation to FIG. 5. In the exemplary embodiments in accordance with FIGS. 6 and 7, the RFID transponder 20 is also integrated into the endoscope 10 in the proximal end region, without this requiring a modification of the outer contour of the endoscope 10. The RFID transponder 20 is likewise not visible from the outside and a reading range of e.g. 30 cm is likewise achievable. In the exemplary embodiments shown in FIGS. 6 and 7, the RFID transponder 20 also surrounds the beam path of the endoscope 10, said beam path being defined by the optical system 24 and the window 13, and it is arranged symmetrically in relation thereto.

All reference signs are not depicted in all figures for reasons of clarity. Reference signs not explained in relation to one figure have the same meaning as in the other figures.

The invention claimed is:

1. An RFID transponder for a medical instrument and/or for an endoscope, comprising,
    at least one printed circuit board carrying an antenna embodied as at least one conductor track of the printed circuit board and an RFID circuit coupled to the antenna,
    wherein the at least one printed circuit board has a ring-shaped embodiment,
    wherein the at least one conductor track is embodied on a radially extending surface of the printed circuit board, and
    wherein the antenna is embodied as a Morgain dipole curved in a ring-shaped manner at least in sections.

2. The RFID transponder as claimed in claim 1, wherein the RFID transponder is embodied as a passive UHF transponder.

3. The RFID transponder as claimed in claim 1, wherein the printed circuit board is embodied as a ring with a break, in particular as a circular ring with one break.

4. The RFID transponder as claimed in claim 3, wherein the RFID transponder is embodied as a ring with a break, in particular as a circular ring with one break.

5. The RFID transponder as claimed in claim 1, wherein the antenna is embodied as a dipole antenna, in particular as a ring dipole.

6. The RFID transponder as claimed in claim 1, wherein the at least one conductor track is folded, at least in sections.

7. The RFID transponder as claimed in claim 1, wherein the RFID circuit is coupled to the antenna by way of a coupling loop.

8. The RFID transponder as claimed in claim 7, wherein the at least one printed circuit board has a first side and a second side, wherein the antenna is arranged on the first side and the coupling loop is arranged on the second side.

9. The RFID transponder as claimed in claim 7, wherein the antenna and the coupling loop are arranged opposite one another.

10. The RFID transponder as claimed in claim 7, wherein an axial distance between the antenna and the coupling loop is adapted for the purposes of compensating an active component of an impedance of the RFID circuit.

11. The RFID transponder as claimed in claim 7, wherein the coupling loop is arranged offset in relation to the antenna in a circumferential direction for the purposes of compensating an active component of an impedance of the RFID circuit.

12. The RFID transponder as claimed in claim 1, wherein the at least one printed circuit board has a first side and a second side, wherein the antenna is arranged on the first side and the RFID circuit is arranged on the second side.

13. An endoscope comprising
    an RFID transponder including at least one printed circuit board carrying an antenna embodied as at least one conductor track of the printed circuit board and an RFID circuit coupled to the antenna,
    wherein the at least one printed circuit board has a ring-shaped embodiment, wherein the at least one conductor track is embodied on a radially extending surface of the printed circuit board, and wherein the antenna is embodied as a Morgain dipole curved in a ring-shaped manner at least in sections.

14. The endoscope as claimed in claim 13, wherein the RFID transponder is integrated into an eyepiece cup of the endoscope and surrounds a beam path of the endoscope in a ring-shaped manner.

15. An assembly method for a medical instrument and/or an endoscope comprising:

inserting an RFID transponder into a ring-shaped groove of at least one component of the medical instrument or endoscope, the RFID transponder including at least one printed circuit board carrying an antenna embodied as at least one conductor track of the printed circuit board and an RFID circuit coupled to the antenna, wherein the at least one printed circuit board has a ring-shaped embodiment, wherein the at least one conductor track is embodied on a radially extending surface of the printed circuit board, and wherein the antenna is embodied as a Morgain dipole curved in a ring-shaped manner at least in sections.

16. A medical instrument comprising, an RFID transponder including at least one printed circuit board carrying an antenna embodied as at least one conductor track of the printed circuit board and an RFID circuit coupled to the antenna, wherein the at least one printed circuit board has a ring-shaped embodiment, wherein the at least one conductor track is embodied on a radially extending surface of the printed circuit board, and wherein the antenna is embodied as a Morgain dipole curved in a ring-shaped manner at least in sections.

17. The medical instrument as claimed in claim 16, wherein the RFID transponder is embodied as a passive UHF transponder.

18. The medical instrument as claimed in claim 16, wherein the printed circuit board is embodied as a ring with a break, in particular as a circular ring with one break.

19. The medical instrument as claimed in claim 18, wherein the RFID transponder is embodied as a ring with a break, in particular as a circular ring with one break.

* * * * *